(12) United States Patent
Drake et al.

(10) Patent No.: US 7,684,047 B2
(45) Date of Patent: Mar. 23, 2010

(54) APPARATUS AND METHOD FOR TWO WAVE MIXING (TWM) BASED ULTRASONIC LASER TESTING

(75) Inventors: Thomas E. Drake, Fort Worth, TX (US); Marc Dubois, Keller, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 678 days.

(21) Appl. No.: 11/553,485

(22) Filed: Oct. 27, 2006

(65) Prior Publication Data

US 2008/0316498 A1    Dec. 25, 2008

(51) Int. Cl.
 *G01B 11/02* (2006.01)
(52) U.S. Cl. ...................................... 356/502
(58) Field of Classification Search ......... 356/484–486, 356/502
See application file for complete search history.

(56) References Cited

U.S. PATENT DOCUMENTS

| | | | | |
|---|---|---|---|---|
| 4,379,633 | A * | 4/1983 | Bickel et al. | 356/502 |
| 4,966,459 | A * | 10/1990 | Monchalin | 356/502 |
| 5,619,326 | A * | 4/1997 | Takamatsu et al. | 356/487 |
| 5,900,935 | A * | 5/1999 | Klein et al. | 356/502 |
| 6,108,087 | A * | 8/2000 | Nikoonahad et al. | 356/503 |
| 6,552,803 | B1 * | 4/2003 | Wang et al. | 356/503 |
| 6,711,954 | B2 * | 3/2004 | Drake, Jr. | 73/655 |
| 7,116,428 | B2 * | 10/2006 | Sauerland et al. | 356/502 |
| 7,463,363 | B2 * | 12/2008 | Drake et al. | 356/502 |
| 7,474,411 | B2 * | 1/2009 | Dubois et al. | 356/502 |
| 2005/0083535 | A1 * | 4/2005 | Kamshilin et al. | 356/502 |
| 2005/0099634 | A1 * | 5/2005 | Dubois et al. | 356/502 |

* cited by examiner

*Primary Examiner*—Gregory J Toatley, Jr.
*Assistant Examiner*—Scott M Richey
(74) *Attorney, Agent, or Firm*—Bracewell & Giuliani LLP

(57) ABSTRACT

A system and method for detecting ultrasonic surface displacements at a remote target are disclosed, one embodiment of the system comprising: a first laser to generate a first laser beam. The first laser beam produces ultrasonic surface displacements on a surface of the remote target. A second laser generates a second laser beam operable to detect the ultrasonic surface displacements on the surface of the remote target and to provide a reference beam to an interferometer. The second laser beam is split, at a beam-splitter, into a pump beam and a probe beam. The pump beam is amplified by a first amplifier and the probe beam is amplified by a second amplifier. The pump beam is then provided to the interferometer as a reference beam and the probe beam is directed to the target to detect the ultrasonic surface displacements. The first and second amplifiers can be controlled independently of one another to control their respective laser beam's power. Collection optics collect phase modulated light from the probe beam either reflected or scattered by the remote target, which can be optionally optically processed to increase the light intensity. The interferometer is a TWM interferometer that receives and processes the phase modulated light and generates at least one output signal based on the phase-modulated light and the amplified reference laser beam.

27 Claims, 5 Drawing Sheets

APPARATUS AND METHOD FOR TWO WAVE MIXING (TWM) BASED ULTRASONIC LASER TESTING

RELATED APPLICATIONS

This application incorporates by reference and claims the benefit of U.S. Provisional Application No. 60/091,240 filed on 30 Jun. 1998 for all purposes.

This application incorporates by reference and claims the benefit of U.S. Provisional Application No. 60/091,229 filed on 30 Jun. 1998 entitled "METHOD AND APPARATUS FOR DETECTING ULTRASONIC SURFACE DISPLACEMENTS USING POST-COLLECTION OPTICAL AMPLIFICATION" to Thomas E. Drake.

This application incorporates by reference and claims the benefit of U.S. patent application Ser. No. 10/753,208 filed on 7 Jan. 2004 and entitled "REMOTE LASER BEAM DELIVERY SYSTEM AND METHOD FOR USE WITH A ROBOTIC POSITIONING SYSTEM FOR ULTRASONIC TESTING PURPOSES" to Thomas E. Drake.

This application incorporates by reference and claims the benefit of U.S. patent application Ser. No. 10/634,342 filed on 12 Feb. 2004 and entitled "METHOD AND APPARATUS FOR ULTRASONIC LASER TESTING" to Thomas E. Drake.

TECHNICAL FIELD OF THE INVENTION

The present invention relates generally to an apparatus and method of non-destructive evaluation of materials, and more particularly, to an apparatus and method of processing optical information to detect ultrasonic surface displacements using an independently-amplified two wave mixing (TWM) photorefractive interferometer to perform a non-destructive evaluation of a material.

BACKGROUND OF THE INVENTION

In recent years, the use of advanced composite structures has experienced tremendous growth in the aerospace, automotive, and many other commercial industries. While composite materials offer significant improvements in performance, they require strict quality control procedures in both the manufacturing processes and after the materials are in service in finished products. Specifically, non-destructive evaluation (NDE) methods must be used to assess the structural integrity of composite materials. This assessment detects inclusions, delaminations and porosities. Conventional NDE methods are slow, labor-intensive, and costly. As a result, testing procedures adversely increase the manufacturing costs associated with composite structures.

Various methods and apparatuses have been proposed to assess the structural integrity of composite structures. One solution uses an external source to generate ultrasonic surface displacements in a work piece which are then measured and analyzed. Often, the external source used to generate the ultrasonic displacements is a pulsed laser beam directed at the work piece. Laser light from a separate detection laser is scattered by the ultrasonic surface displacements created at the work piece. Collection optics then collect the scattered laser energy. The collection optics are coupled to an interferometer or other device, and data about the structural integrity of the composite structure can be obtained through analysis of the scattered laser energy.

Laser ultrasound has been shown to be very effective for the inspection of parts during the manufacturing process. In particular, laser ultrasonic testing systems incorporating a two-wave mixing photorefractive interferometer ("TWM") exhibit advantages over other optical devices for optical demodulation of ultrasonic signals, such as a Fabry-Perot ("FP") interferometer. The TWM interferometer is more compact and less sensitive to vibrations than the FP interferometer, making the TWM interferometer a better choice for mobile and/or in-field laser-ultrasonic systems.

However, one difficulty with the TWM interferometer is that it requires a reference (or pump) beam in addition to a probe (detection) beam to work. The pump beam must be generated by the same laser source as the probe beam. Moreover, the pump beam typically has peak powers between 10's and 100's of watts for scanning applications. These peak powers make the transmission of the pump beam through an optical fiber difficult over large distances due to effects like stimulated Brillouin scattering. This difficulty of transmitting the pump beam over long fiber distances can be worked around by positioning the TWM interferometer close to the laser source (detection laser). However, such an effective proximity cannot be easily obtained for scanning systems where the space around the detection laser is limited. The injection of a high peak power pump beam into an optical fiber is also a concern because the optical fiber can be damaged by the high powered beam if a misalignment occurs.

Another problem with having a high power pump beam is that power must be diverted from the probe beam to supply the pump beam. Therefore, the more power is diverted to the pump beam, the less power goes to the probe beam. The signal-to-noise ratio of the detected ultrasonic waves is dependent on the amount of light (power) of the probe beam. Therefore, the detection laser power diverted into the pump beam decreases the quality of the ultrasonic signals.

Further, in existing TWM interferometer laser ultrasonic detection systems, the level of pump beam power cannot be controlled independently of the probe beam power and the power of the pump beam influences the time-response of the photorefractive crystal and also contributes to background noise on the detector.

SUMMARY OF THE INVENTION

The embodiments of the apparatus and method for two wave mixing (TWM) based ultrasonic laser testing of the present invention substantially address the above identified needs as well as others. More specifically, embodiments of the present invention provide a TWM interferometer laser ultrasonic detection system that can reduce or eliminate the problems associated with the prior art; in particular, the problem of not being able to independently control the power of the probe and pump beams.

One embodiment of the system includes a first (generation) laser to generate a first laser beam. The first laser beam produces ultrasonic surface displacements on a surface of the remote target. A second (detection) laser generates a second laser beam operable to detect the ultrasonic surface displacements on the surface of the remote target and to provide a reference beam to an interferometer. The second laser beam is split, at a beam-splitter, into a pump beam and a probe beam. The pump beam is amplified by a first amplifier and the probe beam is amplified by a second amplifier. The pump beam is then provided to the interferometer as a reference beam and the probe beam is directed to the target to detect the ultrasonic surface displacements. The first and second amplifiers can be controlled independently of one another to control their respective laser beam's power. Collection optics collect phase modulated light from the probe beam either reflected or scattered by the remote target, which can be optionally optically processed to increase the light intensity. The interferometer is a TWM interferometer that receives and processes the phase modulated light and generates at least one output signal based on the phase-modulated light and the amplified reference laser beam. A processor processes the at least one output signal and obtains data representative of the ultrasonic surface displacements on the surface of the remote target. The laser beam can be a pulsed laser beam.

The first amplifier and the second amplifier can be selected from the group consisting of a flash-lamp pumped amplifier, a diode-pumped amplifier, a pulsed amplifier, a continuous-wave amplifier, a rod amplifier, a slab amplifier, and an optical fiber amplifier. The first and second amplifiers can each comprise one or more amplification stages. The interferometer can be remotely located from the detection laser source to enable a distributed architecture.

In another embodiment, a method for detecting ultrasonic displacements at a remote target in accordance with the present invention comprises: splitting a detection laser beam into a reference laser beam and a probe laser beam; amplifying the reference laser beam at a first amplifier; amplifying the probe laser beam at a second amplifier; directing the amplified probe laser beam to the remote target, where the ultrasonic displacements at the remote target scatter the amplified probe laser beam to produce phase-modulated light; collecting the phase modulated light at a collection optic; providing the amplified reference laser beam and the phase-modulated light to an interferometer; and generating at least one output signal at the interferometer based on the phase-modulated light and the amplified reference laser beam, wherein the at least one output signal is representative of the ultrasonic displacements at the remote target.

Still another embodiment of the system for detecting ultrasonic displacements at a remote target of the present invention comprises: a beam splitter to split a detection laser beam into a reference laser beam and a probe laser beam; a first amplifier to amplify the reference laser beam; a second amplifier to amplify the probe laser beam; an optical assembly to receive and direct the amplified probe laser beam to the remote target where the ultrasonic displacements at the remote target scatter the amplified probe laser beam to produce phase-modulated light; collection optics to collect the phase modulated light; and an interferometer to receive the amplified reference laser beam and the phase-modulated light and to generate at least one output signal based on the phase-modulated light and the amplified reference laser beam, wherein the at least one output signal is representative of the ultrasonic displacements at the remote target.

A technical advantage of the present invention is that an improved method for ultrasonic laser testing is provided that allows for more efficient distribution of the different devices in a laser-ultrasonic testing system than prior art such systems. The present invention further provides for independent control of the laser power provided in the pump beam, allowing for desired photorefractive crystal speeds and improved signal-to-noise ratios. The present invention provides a flexible, accurate and cost effective method for inspecting complex composite structures.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGs., like numerals being used to refer to like and corresponding parts of the various drawings.

Embodiments of the present invention provide an improved system, apparatus and method for ultrasonic laser testing using an independently-amplified two wave mixing (TWM) interferometer reference (pump) beam. Unlike prior art ultrasonic laser testing systems using a TWM interferometer, the embodiments of the present invention can thus provide an independent way to control the power of the pump beam to obtain desired photorefractive crystal speeds and background noise levels. The embodiments of the present invention can significantly reduce the amount of power diverted from the detection laser beam to improve the signal-to-noise ratio of the detected ultrasonic signals. Further, embodiments of the present invention provide for a more reliable coupling of the pump beam into an optical fiber and provide for more efficient distribution of the different components of an ultrasonic laser testing system.

Figure 1:
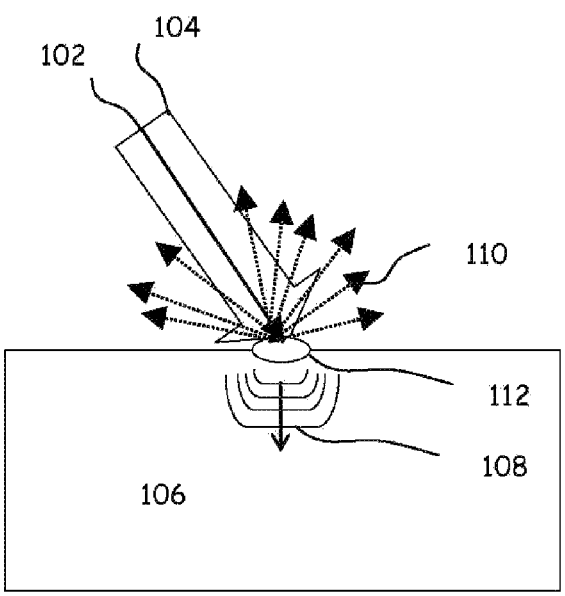
FIG. 1 illustrates the use of a generation laser beam and a detection laser beam to generate and detect laser ultrasonic displacements in accordance with an embodiment of the present invention.

FIG. 1 depicts two incoming laser beams that generate and detect laser ultrasonic displacements as provided by embodiments of the present invention. Laser beam 102 generates ultrasound while illumination (detection) laser beam 104 detects the ultrasound at a remote target 106, such as a composite material under test. As shown, these lasers may be coaxially applied to remote target 106. Generation laser beam 102 causes thermo-elastic expansion 112 in target 106 that results in the formation of ultrasonic deformations or waves 108. Deformations or ultrasonic waves 108 propagate in target 106 and modulate, scatter and reflect illumination laser beam 104 to produce phase-modulated light 110 directed away from target 106 which is collected and processed to obtain information describing the internal structure of remote target 106.

Figure 2:
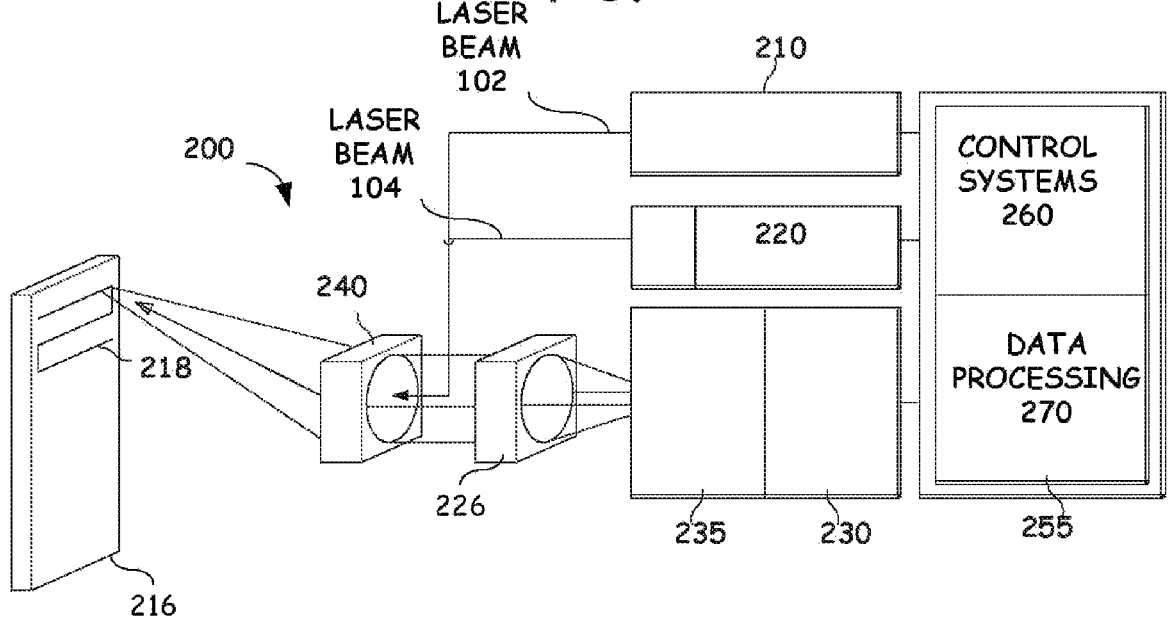
FIG. 2 is a functional block diagram showing the basic components of a laser ultrasonic testing system.

FIG. 2 is a functional block diagram showing the basic components of a system 200 for performing laser ultrasonic testing. Apparatus 200 comprises a generation laser 210, a detection laser 220, an interferometer 230, an optional optical processor 235, an optical scanner 240, collection optics 226, and data processing and control system 255, which can comprise systems controller 260 and data acquisition and processing apparatus 270. Generation laser 210 and detection laser 220 generate a generation laser beam 102 and a detection laser beam 104, respectively, which can be directed by optical scanner 240 upon a target 216, which is typically a composite material. The generation laser 210 produces a compressional ultrasonic wave in the material normal to the surface of the target 216. The compressional ultrasonic wave is the result of thermoelastic expansion of the target 216 composite material as it absorbs generation laser beam 102. System 200 may further include visual cameras, depth cameras, range detectors, narrowband cameras or other like optical sensors known to those having skill in the art.

The generation laser 210 should be of a frequency that is readily absorbed into the surface of target 216 without causing ablation or breaking down the target material, and it must be of the appropriate pulse duration to induce ultrasonic surface deformations. For example, a transverse-excited atmospheric ("TEA") $CO_2$ laser can be used to produce a 10.6 micron wavelength beam for a 100 nanosecond pulse. The power of the laser should be sufficient to deliver, for example, a 0.25 joule pulse to the target, which may require a 100 watt laser operating at a 400 Hz pulse repetition rate. The generation laser beam 102 should be absorbed as heat into the target surface thereby causing thermoelastic expansion without ablation. Although higher-powered generation lasers are not typically used to overcome signal-to-noise ratio ("SNR") issues, as they can result in ablation, in some embodiments, depending on the material being tested, some ablation may be acceptable in order to increase the SNR of the detected signal.

The detection laser 220 should be of sufficient pulse duration to not induce ultrasonic surface displacements. For example, a Nd:YAG laser can be used. The power of this laser should be sufficient to deliver, for example, a 100 milli-joule, 100 micro-second pulse, which may require a one kilo-watt laser.

Detection laser 220 generates detection laser beam 104. Detection laser beam 104 is split into a reference beam and a probe beam, which can then be independently amplified, as will be more clearly described with reference to FIG. 5. Scanner 240 directs the probe beam portion of detection laser 104 to the surface of target 216, which scatters and/or reflects the probe beam portion of detection laser beam 104 to generate phase-modulated light 110. For purposes of this description, "detection laser beam" and "probe beam" may be used interchangeably to mean that portion of the beam generated by detection laser 220 that is directed onto target 216.

Resultant phase-modulated light 110 is collected by collection optics 250. As shown here, scattered and/or reflected phase-modulated light 110 travels through scanner 240 and collection optics 250. Optional optical processor 235 and interferometer 230 process the phase modulated light 110 to produce a signal containing information representative of the ultrasonic displacements at the surface of composite material of target 216. Interferometer 230 can be a two-wave-mixing (TWM) photorefractive interferometer having an independently amplified pulse beam in accordance with the present invention, as will be discussed more fully below with reference to FIGS. 4 and 5. Data processing and control system 255 coordinates operation of the laser ultrasonic system 200 components.

Data processing and control system 255 may comprise a single processing device or a plurality of processing devices. Such a processing device may be a microprocessor, microcontroller, digital signal processor, microcomputer, central processing unit, field programmable gate array, programmable logic device, state machine, logic circuitry, analog circuitry, digital circuitry, and/or any device that manipulates signals (analog and/or digital) based on operational instructions stored in memory. The memory may be a single memory device or a plurality of memory devices. Such a memory device may be a read-only memory, random access memory, volatile memory, non-volatile memory, static memory, dynamic memory, flash memory, cache memory, and/or any device that stores digital information. The memory stores, and data processing and control system 232 executes, operational instructions corresponding to at least some of the steps and/or functions described herein.

Figure 3:
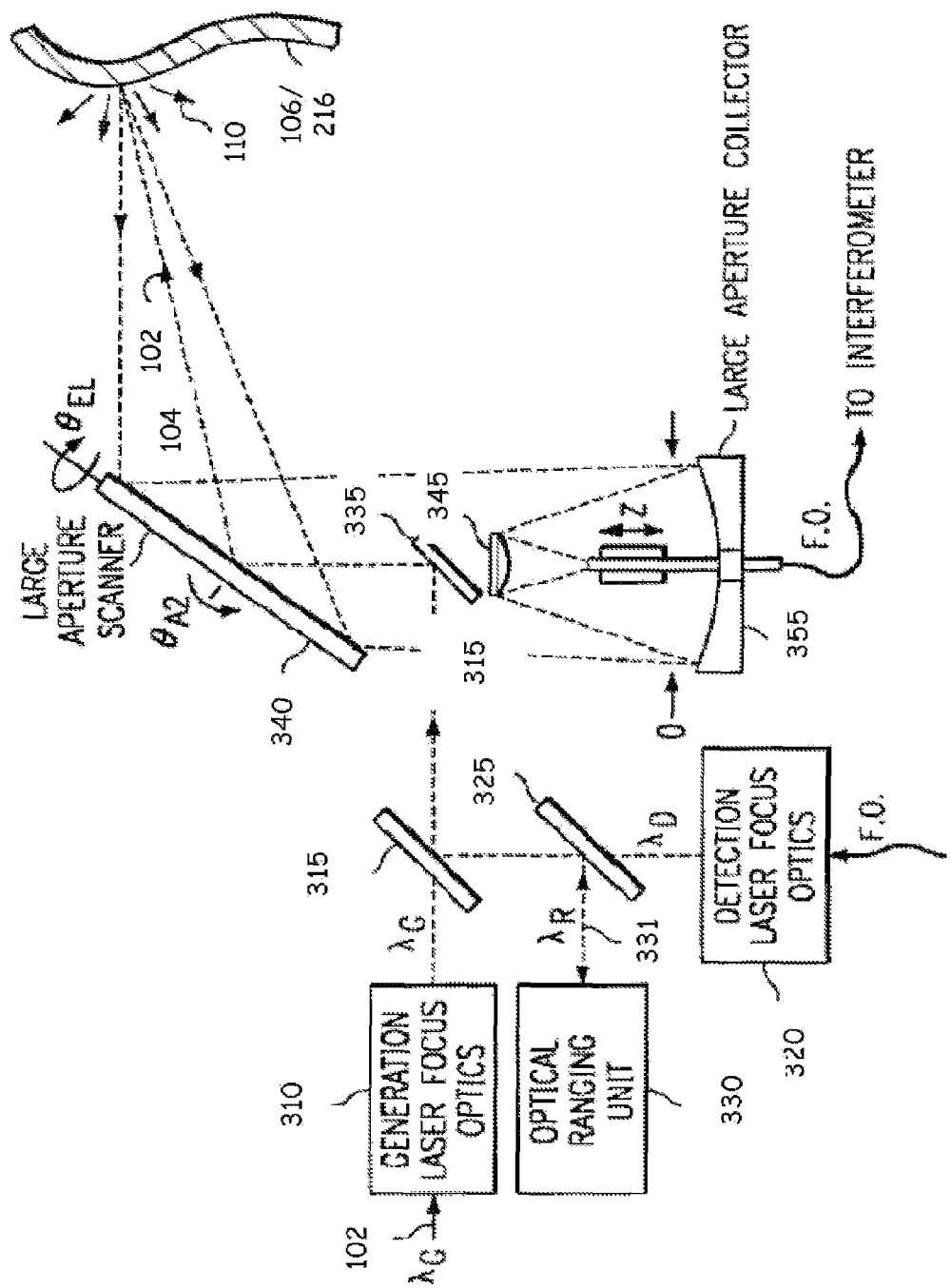
FIG. 3 is a functional block diagram of a large optical scanner that can be used with the embodiments of this invention.

FIG. 3 illustrates a large aperture optical scanning configuration with an integrated distance ranging unit that can be used with the embodiments of the present invention. Generation laser beam 102 is focused by generation laser focus optics 310 through a first optical lens assembly 315 which is transmissive to generation laser beam 102. Reflective surface 335 then directs generation laser beam 102 upon large aperture scanner 340 which, in turn, directs generation laser beam 102 upon a surface of target 216, which induces an ultrasonic wave therein.

As shown in FIG. 3, detection laser beam 104 is directed by fiber optics into detection laser focus optics 320, which focus laser beam 104 through a second optical lens 325 which is transmissive to detection laser beam 104. Detection laser beam 104 is reflected off first optical lens 315 and emerges coaxial with generation laser beam 102. First optical assembly 315 and second optical assembly 325 act collectively to form a beam combiner or beam mixer. Detection laser beam 104 is then reflected along with generation laser beam 102 upon a turning mirror or a reflective surface 335, which then directs detection laser beam 104 upon large aperture scanner 340 which, in turn, directs said beam 104 upon the surface of target 216. Detection laser beam 104 interacts with the ultrasonic waves present in the surface of target 216, and is reflected as phase modulated light 110. Some of the phase modulated light is captured by large aperture scanner 340 and is directed upon large aperture collector 350. Large aperture scanner 340 is generally of the single-mirror two-axis gimbal construction with each axis driven via a motor and gear assembly. Large aperture collector 350 may be of a Cassegrain-type reflective optic, comprised of a primary reflective surface 355 which focuses light upon a secondary reflective surface 345, which in turn, collects the light and focuses it into a fiber optic carrier.

FIG. 3 also illustrates an integrated optical ranging unit 330 which directs a ranging laser beam 331 upon optical lens 325, which reflects said laser beam 331 upon first optical lens 315. Ranging laser beam 331 emerges coaxial with generation laser beam 102 and detection laser beam 104. Ranging laser beam 331 is then reflected along the same path as detection laser beam 104 and also is reflected from the surface of target 216. Some of the reflected ranging laser is captured by large aperture scanner 340 and directed backwards upon the same path which it traveled to reach target 216.

Scanner 340, collection optics 345 and 355 are generally defined as of the large aperture type for beam clear apertures larger than approximately 75 mm for distances to the target in the 1000 mm to 4000 mm range. Embodiments of the present invention can instead in some instances comprise a small aperture scanning configuration with an integrated distance ranging unit. Optical ranging unit 330 is able to determine from the reflected light the distance between the surface of the target 216 being illuminated and the scanning apparatus. Because optical ranging unit 330 both transmits and receives light of the same frequency, it is described as a self-contained ranging apparatus. It is important to know the distance by which the surface being illuminated is located from the scanner so that a topographical contour can be created for target 216 and correlated to the optical data being collected. Generally, this correlation is recorded on a point-by-point basis.

A key aspect of the embodiments of the present invention is the use of a TWM interferometer 230. A TWM interferometer presents advantages over other optical devices for optical demodulation of ultrasonic signals, such as a Fabry-Perot (FP) interferometer. The TWM is more compact and less sensitive to vibrations than the FP, making the TWM a better choice for mobile and/or in-field laser-ultrasonic systems. A difficulty with the TWM, however, is that it requires a pump beam, from the same laser source as the probe beam. Moreover, the pump beam requires typical peak powers between 10's and 100's of watts for scanning applications. These peak powers make it difficult to transmit the pump beam through an optical fiber over long distances (e.g., several meters) due to effects like stimulated Brillouin scattering. The injection of large peak powers into an optical fiber is also a concern because the fiber can be damaged by high peak powers if a misalignment occurs.

Another problem with having a high power pump beam is that power must be diverted from the probe beam to supply the pump beam. Therefore, the more power is diverted to the pump beam, the less power goes to the probe beam. The signal-to-noise ratio of the detected ultrasonic waves is dependent on the amount of light (power) of the probe beam. Therefore, the detection laser power diverted into the pump beam decreases the quality of the ultrasonic signals. Lastly, in prior art TWM interferometer laser ultrasonic detection systems, the level of the pump beam power cannot be controlled independently of the probe beam power.

Another difficulty arises with the prior-art approach if some optical processing is required on either the pump or probe beam independently one from the other. An example of such optical processing is an optical frequency shift to compensate for the Doppler effect undergone by the probe beam when this latter is scanned at the surface of a sample, as shown in FIG. 2. An example of that optical processing is shown in "*Doppler Frequency-Shift Compensated Photorefractive Interferometer for Ultrasound Detection on Objects in Motion*" by B. Campagne et al., in Review of Progress in QNDE, vol. 22, 2003, p. 273, which is incorporated by reference. Such optical processing is rendered difficult when carried out with the amplified beam because of the relatively low quality of the beam (coming either directly from the amplifier or from a large multimode fiber required for large peak powers). Those difficulties very often result in an additional loss of power, further decreasing the probe beam power reaching the target, and hence further decreasing the SNR.

Figure 4:
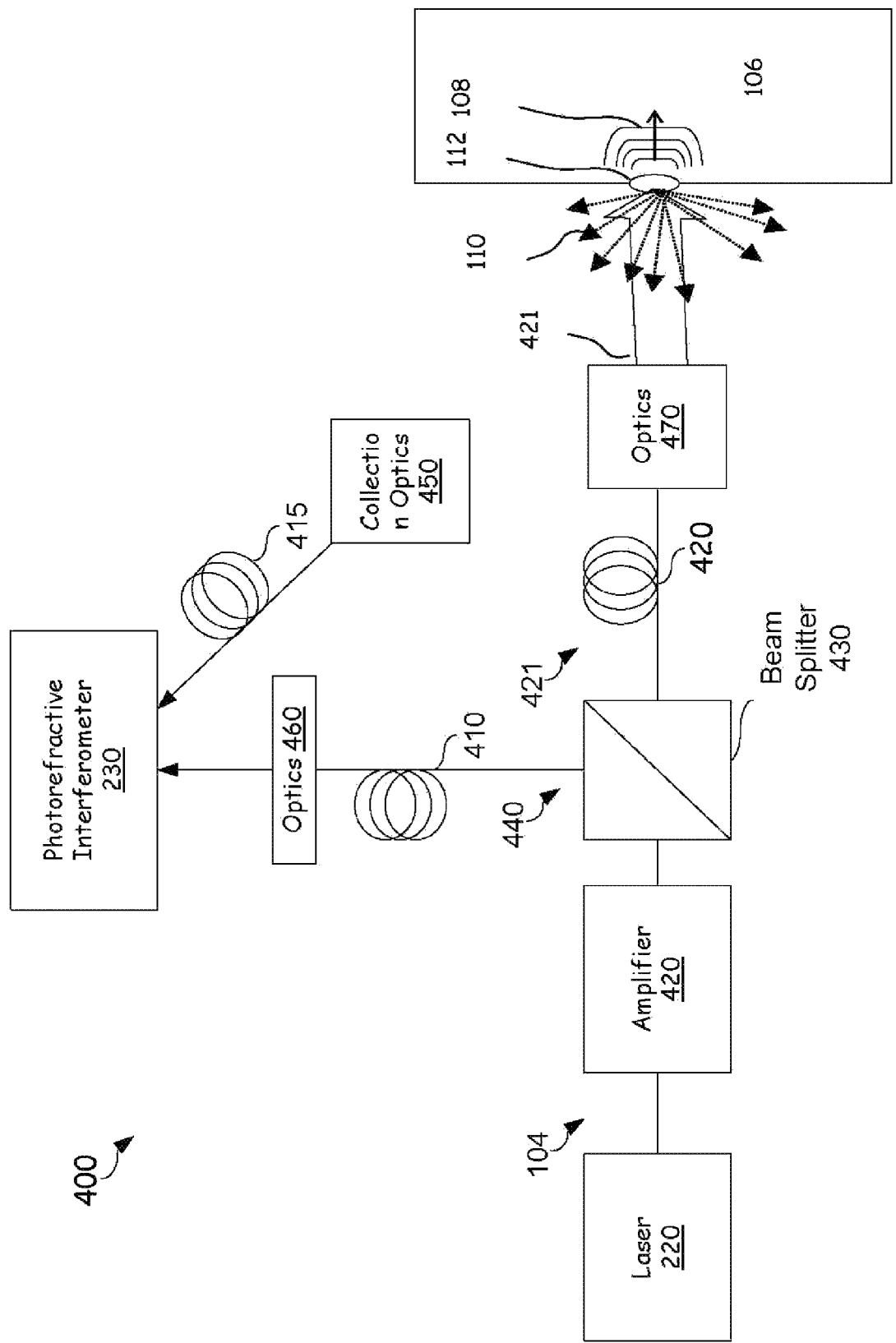
FIG. 4 is a functional block diagram of a prior art ultrasonic testing system having a single amplifier for both the probe and pump beams.

FIG. 4 is a functional block diagram of a prior art ultrasonic testing system 400 having a single amplifier 420 for amplifying both a probe beam and a pump beam. Detection laser 220 generates detection laser beam 104 which is provided to amplifier 420. Amplifier 420 amplifies the detection laser beam 104 and provides the amplified detection laser beam 104 to beam splitter 430, which splits the detection laser beam 104 into probe beam 421 (which is operable to detect ultrasonic disturbances at target 106/216 as described above with reference to FIGS. 1-3) and pump beam 440, as will be familiar to those having skill in the art. Notice that the beam splitter 430 can be a polarizing cube, a non-polarizing cube, a thin-film plate, a fused optical fiber splitter, or any other device that separates the beam in two according to the desired ratio. Pump beam 440 is provided to TWM 230 via optic 460 and an optical fiber 410. Probe beam 421 can be directed to target 216 via an optic 470 and another optical fiber 420. Phase-modulated light 110 is collected via optics 450 (collection optics 250 of FIG. 2) and provided to TWM 230 by, for example, an optical fiber 415. In this prior art ultrasonic laser testing system, the pump beam 440 and probe beam 421 are created downstream of the laser amplifier 420. The pump beam 440 power is thus limited by the required length of the optical fiber 410 and the probe beam 421 has its power diminished by an amount at least equal to that of the pump beam 440 power. Pump beam 440 and probe beam 421 power levels cannot be controlled independently of one another. These conditions are undesirable for the reasons discussed above.

Figure 5:
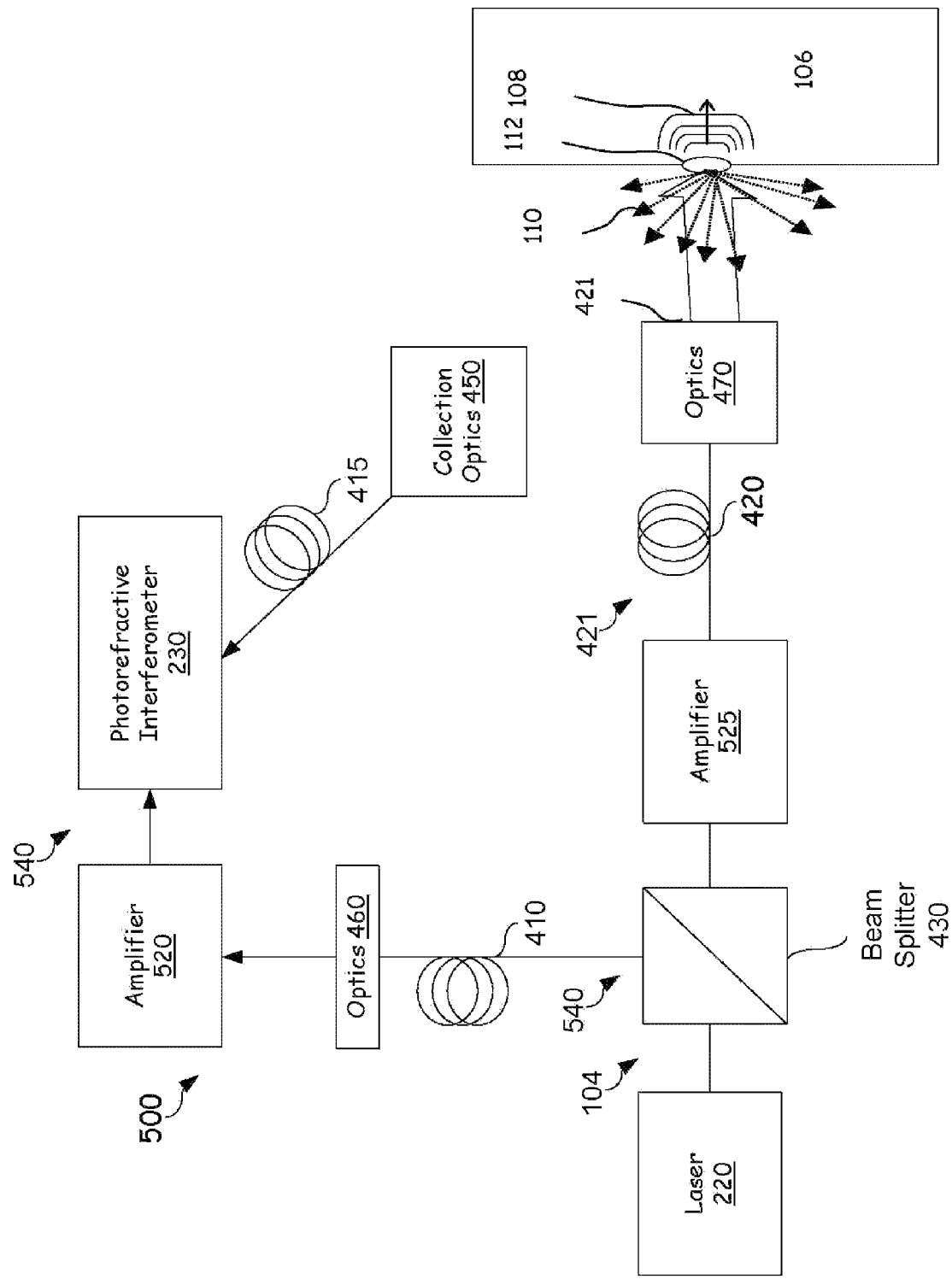
FIG. 5 is a functional block diagram of an embodiment of the present invention having separate optical amplifiers for the probe and pump beams.

FIG. 5 is a functional block diagram of an embodiment of the present invention having separate optical amplifiers for the probe and pump beams. As in FIG. 4, ultrasonic laser testing system 500 comprises a detection laser 220, which generates detection laser beam 104. Unlike the prior art, detection laser beam 104 is provided to beam splitter 430 prior to being amplified. Beam splitter 430 splits the detection laser beam 104 into probe beam 521 (which is operable to detect ultrasonic disturbances at target 216 as described above with reference to FIGS. 1-4) and pump beam 540, in a manner analogous to that of system 400 of FIG. 4. Pump beam 540 is provided to an amplifier 520 via an optical fiber 410 and an optic 460. Amplifier 520 then provides an amplified pump beam 540 to TWM 230. Probe beam 521 is provided to a separate amplifier 525 by beam splitter 430 where it is separately amplified before being directed to target 216 via an optic 470 and another optical fiber 420. Phase-modulated light 110 is collected via optics 450 (collection optics 250 of FIG. 2) and provided to TWM 230 by optical fiber 415 as before.

Amplifiers 520 and 525 of the embodiments of the present invention provide the ability to independently amplify pump beam 540 and probe beam 521, respectively. Further, each of amplifiers 520 and 525 can comprise, in some embodiments, multiple amplifiers as may be desired for a given application. The embodiments of the present invention can thus reduce or eliminate the problems of prior art TWM-based ultrasonic laser testing systems such as that of FIG. 4.

Typically, the detection laser source 220 for a laser-ultrasonic detection system has 10's to 100's of milliwatts of power. These levels of laser beam power can be easily split and sent over long distances through optical fibers. Because the pump beam 540 has its own dedicated amplifier, the TWM can be located far away from the detection laser enabling a distributed architecture.

An embodiment of the present invention, such as that of FIG. 5, can provide the ability to control the pump beam power independently from the probe beam and very little if any of the original detection laser beam 104 power is lost from the probe beam 521 because probe beam amplifier 525 is operable to amplify the probe beam 521 as needed.

The two amplifiers 520 and 525 for the pump beam 540 and probe beam 521, respectively, can be of different types. Typically for the probe beam 521, a pulsed bulk amplifier can be used to provide very high peak power. For the pump beam 540, an amplifier of lower peak power can be used. The amplifiers 520 and 525 can be any combination of, but not limited to, single or multiple amplifiers of the following types: flash-lamp pumped amplifiers, diode-pumped amplifiers, pulsed amplifiers, continuous-wave amplifiers, rod amplifiers, slab amplifiers, or optical fiber amplifiers.

An additional advantage of the embodiment shown in FIG. 5 is the ability to do some optical processing on the reference and/or detection beam before amplification. An example of such optical processing is an optical frequency shift to compensate for the Doppler effect undergone by the probe beam when this latter is scanned at the surface of a sample, as shown in FIG. 2. Before amplification, the probe and pump beams are usually of very high quality, either coming directly from the detection laser source 220 or coming out of a small-diameter single-mode fiber. Less power is lost during this optical processing because of the better beam quality but even though some power is still lost, the post-optical processing amplification might still produce the full power if the amplifier is operated in saturation.

Figure 6:
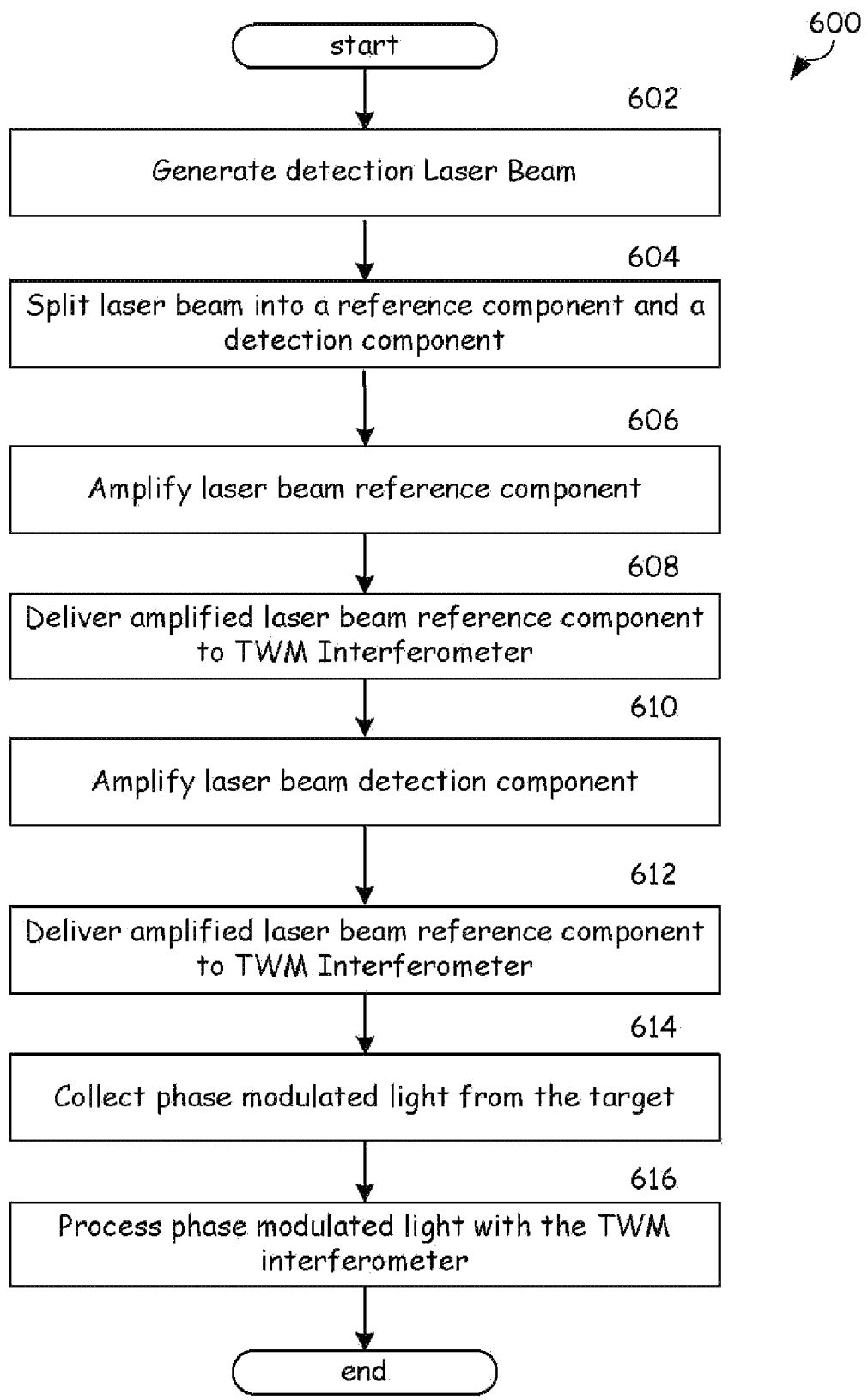

FIG. 6 provides a logic flow diagram in accordance with embodiments of the present invention for detecting ultrasonic displacements at a remote target in accordance with embodiments of the present invention. Operations 600 begin with Step 602. In Step 602 a detection laser beam may be generated using a laser source. In Step 604 the laser beam may be split into a reference component and a detection component. The reference component may be supplied to a two wave mixing (TWM) interferometer. In Step 606 the referenced component of the laser beam may be independently amplified from that of the detection component. In Step 608 the amplified laser beam component is delivered to TWM interferometer. Simultaneously in Step 610 the laser beam detection component may be independently amplified from that of the reference component. In Step 612 the amplified laser beam detection component may be delivered to a target. Step 614 collects phase modulated light from the target. This phase modulated light may be generated by ultrasonic displacement as discussed with reference to FIG. 1. In Step 616 the phase modulated light may be processed with the TWM interferometer. The TWM interferometer utilizes both the phase modulated light collected and the laser beam reference component to generate information about the ultrasonic displacements at the target. This information may then be further processed to determine internal structure of the remote target.

The embodiments of the present invention can thus offer an improved ultrasonic laser testing system by providing for the efficient distribution of the different components required for a laser-ultrasonic system. The embodiments of the present invention make the injection of the pump beam into an optical fiber much more reliable. Further, the embodiments of the present invention provide an independent way to control the power in the pump beam in order to obtain desired photorefractive crystal speeds and background noise levels and can compensate for the laser beam power diverted from the detection beam 104 to maintain the maximum level of signal-to-noise ratio for the detected ultrasonic signals. Also, the embodiments of the present invention offer the ability to carry out optical processing on either the probe or pump beam independently one from the other much more efficiently by using the beams before amplification.

In operation, the embodiments of the present invention allow laser ultrasonic test equipment to be used in a wider range of environments while testing more complex surfaces or surfaces within limited access areas. The present invention also allows existing laser ultrasound equipment to be modified to test more complex surfaces or surfaces within limited access areas without replacing the existing detection laser, an expensive component in the laser ultrasound system. The ultrasonic laser systems described herein are exemplary, and the embodiments of the present invention can be implemented within any ultrasonic laser testing system having a TWM interferometer.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention has been described in detail, it should be understood that various changes, substitutions and alterations can be made hereto without departing from the spirit and scope of the invention as defined by the appended claims.

What is claimed is:

1. A laser ultrasonic inspection system operable to detect ultrasonic displacements at a remote target, comprising:
   a generation laser source operable to generate a generation laser beam, wherein the generation laser beam is directed onto the remote target to produce ultrasonic displacements at the remote target;
   a detection laser source operable to generate a detection laser beam;
   a beam splitter for splitting the detection laser beam into a probe laser beam and a reference laser beam;
   a first amplifier to amplify the reference laser beam;
   a second amplifier to amplify the probe laser beam;
   an optical assembly that receives and directs the amplified probe laser beam to the remote target where the ultrasonic displacements at the remote target scatter the amplified probe laser beam to produce phase-modulated light;
   collection optics to collect the phase modulated light;
   an interferometer to receive the amplified reference laser beam and the phase-modulated light and to generate at least one output signal based on the phase-modulated light and the amplified reference laser beam; and
   a processor operable to process the at least one output signal to obtain data representative of the ultrasonic displacements at the remote target.

2. The system oil claim 1, wherein the first amplifier and the second amplifier are selected from the group consisting of a flash-lamp pumped amplifier, a diode-pumped amplifier, a pulsed amplifier, a continuous-wave amplifier, a rod amplifier, a slab amplifier, and an optical fiber amplifier.

3. The system of claim 1, wherein the first amplifier and the second amplifier can be controlled independently of one another to control the power of the reference laser beam and the probe laser beam.

4. The system of claim 1, wherein the interferometer is a two-wave mixing photorefractive interferometer ("TWM").

5. The system of claim 1, wherein the interferometer can be remotely located form the detection laser source to enable a distributed, architecture.

6. The system of claim 1, wherein the first and second amplifiers can each comprise one or more amplification stages.

7. The system of claim 6, wherein the first and second amplifiers can each be comprised by a combination of pulsed and continuous-wave amplification stages.

8. The system of claim 1, wherein the remote target comprises a composite material.

9. The system of claim 1, wherein the reference and the probe laser beam are optically processed independently for scanning applications.

10. A system for detecting ultrasonic displacements at a remote target, comprising:
- a beam splitter to split a detection laser beam into a reference laser beam and a probe laser beam;
- a first amplifier to amplify the reference laser beam;
- a second amplifier to amplify the probe laser beam;
- an optical assembly to receive and direct the amplified probe laser beam to the remote target where the ultrasonic displacements at the remote target scatter the amplified probe laser beam to produce phase-modulated light;
- collection optics to collect the phase modulated light; and
- an interferometer to receive the amplified reference laser beam and the phase-modulated light and to generate at least one output signal based on the phase-modulated light and the amplified reference laser beam, wherein the at least one output signal is representative of the ultrasonic displacements at the remote target.

11. The system of claim 10, wherein the first amplifier and the second amplifier are selected from the group consisting of a flash-lamp pumped amplifier, a diode-pumped amplifier, a pulsed amplifier, a continuous-wave amplifier, a rod amplifier, a slab amplifier, and an optical fiber amplifier.

12. The system of claim 10, wherein the first amplifier and the second amplifier can be controlled independently of one another to control the power of the reference laser beam and the probe laser beam.

13. The system of claim 10, wherein the interferometer is two-wave mixing photorefractive interferometer ("TWM").

14. The system of claim 10, wherein the interferometer can be remotely located from the detection laser source to enable a distributed architecture.

15. The system of claim 10, wherein the first and second amplifiers can each comprise one or more amplification stages.

16. The system of claim 15, wherein the first and second amplifiers can each be comprised by a combination of pulsed and continuous-wave amplification stages.

17. The system of claim 10, wherein the remote target comprises a composite material.

18. The system of claim 10, wherein the reference or the probe laser beam or both are optically processed independently one from the other for scanning applications.

19. A method for detecting ultrasonic displacements at a remote target, comprising:
- splitting a detection laser beam into a reference laser beam and a probe laser beam;
- amplifying the reference laser beam at a first amplifier;
- amplifying the probe laser beam at a second amplifier;
- directing the amplified probe laser beam to the remote target, where the ultrasonic displacements at the remote target scatter the amplified probe laser beam to produce phase-modulated light;
- collecting the phase modulated light at a collection optic;
- providing the amplified reference laser beam and the phase-modulated light to an interferometer; and
- generating at least one output signal at the interferometer based on the phase-modulated light and the amplified reference laser beam, wherein the at least one output signal is representative of the ultrasonic displacements at the remote target.

20. The method of claim 19, wherein the first amplifier and the second amplifier are selected from the group consisting of a flash-lamp pumped amplifier, a diode-pumped amplifier, a pulsed amplifier, a continuous-wave amplifier, a rod amplifier, a slab amplifier, and an optical fiber amplifier.

21. The method of claim 19, wherein the first amplifier and the second amplifier can be controlled independently of one another to control the power of the reference laser beam and the probe laser beam.

22. The method of claim 19, wherein the interferometer is a two-wave mixing photorefractive interferometer ("TWM").

23. The method of claim 19, wherein the interferometer can be remotely located from the detection laser source to enable a distributed architecture.

24. The method of claim 19, wherein the first and second amplifiers can each comprise one or more amplification stages.

25. The method of claim 24, wherein the first and second amplifiers can each be comprised by a combination of pulsed and continuous-wave amplification stages.

26. The method of claim 19, wherein the remote target comprises a composite material.

27. The method of claim 19, wherein the reference or the probe laser beam or both are optically processed independently one from the other for scanning applications.

* * * * *